United States Patent [19]

Flam

[11] Patent Number: 5,590,643

[45] Date of Patent: Jan. 7, 1997

[54] MANDIBULAR PROTRACTING ORAL INTUBATING AIRWAY

[76] Inventor: Gary H. Flam, 2244 Robinhood, Houston, Tex. 77005

[21] Appl. No.: 373,065

[22] Filed: Jan. 17, 1995

[51] Int. Cl.$^6$ .......................... A61C 5/14; A61M 16/00; A62B 9/06

[52] U.S. Cl. .................. 128/200.26; 128/207.14; 128/201.26; 128/206.29; 128/859; 128/860; 128/861

[58] Field of Search ................. 128/200.26, 201.26, 128/206.29, 207.14, 911, 912, DIG. 26, 859, 861, 848, 860

[56] References Cited

U.S. PATENT DOCUMENTS

| | | | |
|---|---|---|---|
| 1,674,336 | 6/1928 | King | 128/861 |
| 2,669,988 | 2/1954 | Carpenter | 128/848 |
| 3,037,501 | 6/1962 | Miller | 128/206.29 |
| 3,139,088 | 6/1964 | Galleher, Jr. | 128/859 |
| 3,496,936 | 2/1970 | Gores | 128/861 |
| 4,112,936 | 9/1978 | Blachly | 128/207.14 |
| 4,166,467 | 9/1979 | Abramson | 128/207.14 |
| 4,270,531 | 6/1981 | Blachly et al. | 128/207.14 |
| 4,425,911 | 1/1984 | Luomanen et al. | 128/200.26 |
| 4,495,945 | 1/1985 | Liegner | 128/200.26 |
| 4,664,109 | 5/1987 | Rasocha | 128/207.14 |
| 4,944,313 | 7/1990 | Katz et al. | 128/207.14 |
| 5,003,994 | 4/1991 | Cook | 128/848 |
| 5,092,346 | 3/1992 | Hays et al. | 128/848 |
| 5,117,816 | 6/1992 | Shapiro et al. | 128/200.24 |
| 5,203,324 | 4/1993 | Kinkade | 128/861 |
| 5,277,202 | 1/1994 | Hays | 128/848 |
| 5,316,020 | 5/1994 | Truffer | 128/861 |
| 5,409,017 | 4/1995 | Lowe | 128/848 |

Primary Examiner—Kimberly L. Asher
Attorney, Agent, or Firm—Kenneth A. Roddy

[57] ABSTRACT

A mandibular protracting oral intubating airway has a rigid main body with a mouthpiece portion at the forward end. The mouthpiece portion has an annular front flange and a bite portion extending a short distance rearwardly therefrom which is generally oval-shaped in transverse cross section and has an annular rear flange at the rear end thereof. A flat, generally C-shaped tongue retractor portion extends rearwardly from the rear flange of the bite portion and curves downwardly. A resilient annular sleeve encircles the bite portion between the front and rear flanges and has a series of longitudinally spaced generally arcuate grooves extending transversely across its exterior top and bottom surfaces. When properly positioned in the mouth of a patient, the upper and lower teeth are retained in the grooves of the resilient sleeve with the mandible protracted maximally forward relative to the maxilla. This, and the underside of the downwardly curved tongue retractor hold the tip and most of the tongue forward and prevent it from falling backward and obstructing the airway. After the device has been installed, there is no need for continuous manual chin lift or jaw thrust to maintain an open oral airway. The mouthpiece portion functions as a bite block and the oval-shaped opening through the bite portion functions as an intubation guide to facilitate insertion of an endoscope and related medical instruments, such as a fiberoptic intubating stylet with an attached endotracheal tube.

5 Claims, 2 Drawing Sheets

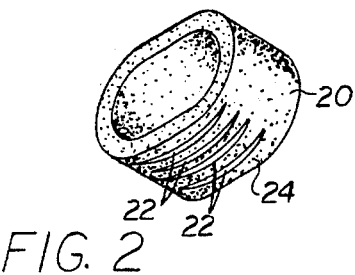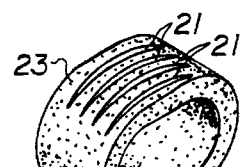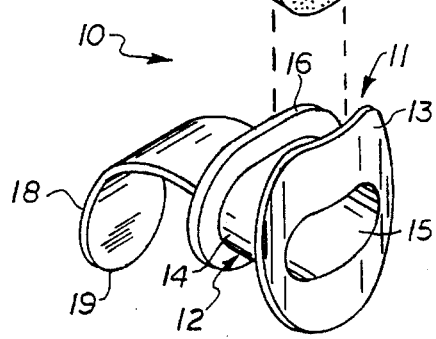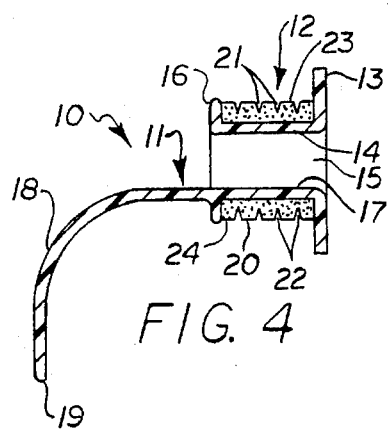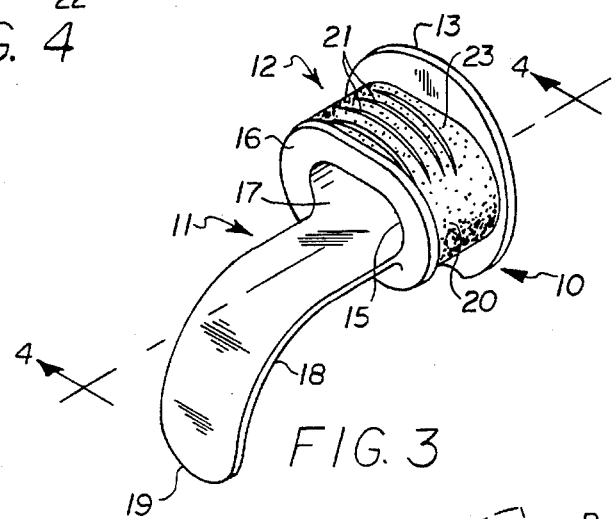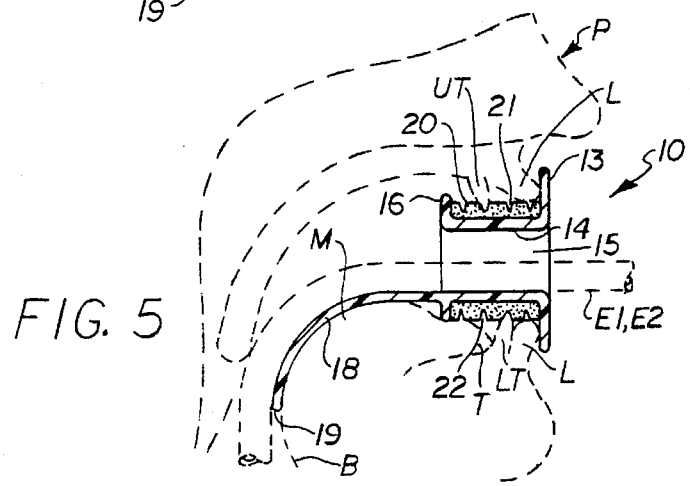

MANDIBULAR PROTRACTING ORAL INTUBATING AIRWAY

FIELD OF THE INVENTION

This invention relates generally to oral airway and intubation devices, and more particularly to a mandibular protracting oral intubating airway which maintains the mandible of a patient in a protracted position and prevents the tongue from falling backward and obstructing the flow of air into the lungs and facilitates the insertion of such devices as an endotracheal tube or endoscope into the upper respiratory or gastrointestinal tracts of the patient.

BRIEF DESCRIPTION OF THE PRIOR ART

For maintenance of safe general anesthesia, unobstructed flow of oxygen and anesthetic gases must occur from the anesthesia circuit and mask all the way to the lungs of the patient and back.

With decreasing levels of consciousness and increased depth of sedation or anesthesia, the tongue tends to fall backward into the throat and progressively obstruct airflow. This is commonly seen in a sleeping patient who is snoring. If not addressed, this can result in complete airway obstruction with death from suffocation.

"Chin lift" and "jaw thrust" are two procedures commonly used in the medical field to maintain an open airway in an unconscious or sedated patient. Both of these procedures involve protracting the mandible or lower jaw by pulling it forward relative to the maxilla or upper jaw. When the mandible or lower jaw is protracted, it pulls the tongue forward with it, so that it tends to obstruct the airway less.

There are certain situations in which moderate to heavy sedation or general anesthesia without endotracheal intubation (insertion of a tube into the trachea) is desired; for example, a "mask general anesthetic" on a patient for a surgical procedure of short duration. In this situation, it is frequently necessary for the anesthesiologist to use a conventional oral airway device along with chin lift or jaw thrust to maintain an unobstructed airway. Prior art conventional oral airway devices act only on the tongue, and not the mandible. This requires the anesthesiologist to use one hand on the patient's jaw and the mask at all times, thus limiting his or her mobility.

Kinnear et al, U.S. Pat. No. 3,756,244; Kossove, U.S. Pat. No. 4,363,320; and Baildon, U.S. Pat. No. 4,919,126 disclose oral airway devices which act only on the tongue, and not the mandible.

There are also some situations when patients under general anesthesia must undergo endotracheal intubation. For example, long operations done on patients in the prone position, and operations on patients who are at increased risk of vomiting or gastroesophageal reflux and pulmonary aspiration of gastric contents. Most of these patients can be intubated after they are asleep using traditional direct laryngoscopy, but if they cannot, another method must be used.

Prior art conventional oral airway devices which are used for fiberoptic oral intubation do not protract the mandible, and still frequently require the jaw thrust maneuver for optimal mask ventilation. Another problem with these prior art devices is that they do not have a short straight channel which allows manipulation of a fiberoptic intubating stylet with an attached endotracheal tube through it. These types of devices are also unsuitable for use in an awake or mildly sedated patient because they are relatively large and their rearward ends pass far into the throat and cause the patient to gag, cough, or even vomit.

Williams, U.S. Pat. No. 4,338,930; Berman, U.S. Pat. No. 4,054,135; and Ovassapian et al, U.S. Pat. No. 5,024,218 disclose intubating airway devices which do not protract the mandible, and have the shortcomings described above.

Annular mouthpieces and bite blocks are known in the art. These devices are used for endoscopic examination of the throat, and upper respiratory and gastrointestinal tracts. However, prior art mouthpieces and bite blocks are unsuitable for use in a moderately sedated or unconscious patient because they are relatively short and do not protract the mandible, nor a significant amount of the tongue.

Katz et al, U.S. Pat. No. 4,944,313 discloses a single use rigid annular mouthpiece for use with a medical instrument such as an endoscope which protects the endoscope from damage and has a compressible deformable member formed of polyolefin which surrounds the rigid portion and merely functions to protect the teeth of the patient and to provide a visual indication as to whether the device has been used previously. Since the compressible deformable member becomes deformed, it would be incapable of maintaining the mandible in a protracted condition.

Jackson, U.S. Pat. No. 5,174,284 discloses a rigid bite block for use with a medical instrument such as an endoscope which protects the endoscope from damage and has sloping top and bottom surfaces which receive the upper and lower teeth of the patient and cause both the upper and lower teeth to slide forward when the patient bites down on the block. The sloping surfaces would be incapable of protracting the mandible relative to the maxilla and maintaining the mandible in the protracted condition.

The present invention is distinguished over the prior art in general, and these patents in particular by a mandibular protracting oral intubating airway having a rigid main body with a mouthpiece portion at the forward end. The mouthpiece portion has an annular front flange and a bite portion extending a short distance rearwardly therefrom which is generally oval-shaped in transverse cross section and has an annular rear flange at the rear end thereof. The bottom wall of the bite portion extends rearwardly from the rear flange and curves downwardly in a flat, generally C-shaped tongue retractor portion. A resilient annular sleeve mounted between the front and rear flanges encircles the bite portion and has a series of longitudinally spaced generally arcuate grooves extending transversely across the exterior of its top and bottom surfaces. When properly positioned in the mouth of a patient, the upper and lower teeth are retained in the grooves of the resilient sleeve with the mandible protracted maximally forward relative to the maxilla, which pulls the base of the tongue forward so that it tends to obstruct the airway less, and the underside of the flat downwardly curved tongue retractor holds the rest of the tongue forward and prevents it from falling backward and obstructing the airway. After the device has been installed, there is no need for continuous manual chin lift or jaw thrust. The mouthpiece portion functions as a bite block and the oval-shaped opening through the bite portion functions as an intubation guide to facilitate insertion of an endoscope and related medical instruments, such as a fiberoptic intubating stylet with an attached endotracheal tube.

SUMMARY OF THE INVENTION

It is therefore an object of the present invention to provide a mandibular protracting oral intubating airway which maintains the airway of an unconscious or sedated patient open to the greatest degree possible.

It is another object of this invention to provide a mandibular protracting oral intubating airway which protracts the mandible or lower jaw relative to the maxilla or upper jaw and pulls the tongue forward with it.

Another object of this invention is to provide a mandibular protracting oral intubating airway which eliminates the need for an anesthesiologist to perform continuous manual chin lift or jaw thrust and frees the hands of the anesthesiologist to perform other tasks.

Another object of this invention is to provide a mandibular protracting oral intubating airway which maintains the airway of an unconscious or heavily sedated patient open to the greatest degree possible for spontaneous or controlled ventilation, while allowing relatively rapid, unencumbered oral fiberoptic intubation using a fiberoptic stylet in patients who cannot be intubated using traditional direct laryngoscopy.

Another object of this invention is to provide a mandibular protracting oral intubating airway which maintains the airway of a patient open to the greatest degree possible and is sufficiently small and compact to be easily tolerated by an awake or mildly sedated patient to reduce the possibility of gagging, coughing, or vomiting.

A further object of this invention is to provide a mandibular protracting oral intubating airway which functions as a bite block for endoscopic examination of the upper gastrointestinal and respiratory tracts and also functions to maintain the airway of a spontaneously breathing sedated or unconscious patient open to the greatest degree possible.

A still further object of this invention is to provide a mandibular protracting oral intubating airway which is simple in construction, economical to manufacture, and is safe and reliable in use.

Other objects of the invention will become apparent from time to time throughout the specification and claims as hereinafter related.

The above noted objects and other objects of the invention are accomplished by a mandibular protracting oral intubating airway having a rigid main body with a mouthpiece portion at the forward end. The mouthpiece portion has an annular front flange and a bite portion extending a short distance rearwardly therefrom which is generally oval-shaped in transverse cross section and has an annular rear flange at the rear end thereof. The bottom wall of the bite portion extends rearwardly from the rear flange and curves downwardly in a flat, generally C-shaped tongue retractor portion. A resilient annular sleeve mounted between the front and rear flanges encircles the bite portion and has a series of longitudinally spaced generally arcuate grooves extending transversely across the exterior of its top and bottom surfaces. When properly positioned in the mouth of a patient, the upper and lower teeth are retained in the grooves of the resilient sleeve with the mandible protracted maximally forward relative to the maxilla, which pulls the base of the tongue forward so that it tends to obstruct the airway less, and the underside of the flat downwardly curved tongue retractor holds the rest of the tongue forward and prevents it from falling backward and obstructing the airway. After the device has been installed, there is no need for continuous manual chin lift or jaw thrust. The mouthpiece portion functions as a bite block and the oval-shaped opening through the bite portion functions as an intubation guide to facilitate insertion of an endoscope and related medical instruments, such as a fiberoptic intubating stylet with an attached endotracheal tube.

BRIEF DESCRIPTION OF THE DRAWINGS

FIG. 1 is an exploded isometric view of a mandibular protracting oral intubating airway in accordance with the present invention shown in an unassembled condition.

FIG. 2 is an isometric view showing the underside of the resilient sleeve of the mandibular protracting oral intubating airway.

FIG. 3 is an exploded isometric view of the mandibular protracting oral intubating airway shown from the rear in an assembled condition.

FIG. 4 is a cross sectional view of the mandibular protracting oral intubating airway taken along line 4—4 of FIG. 3.

FIG. 5 is a side elevation showing the mandibular protracting oral intubating airway in a patient's mouth with the mandible protracted and an endotracheal tube being inserted through the airway.

DESCRIPTION OF THE PREFERRED EMBODIMENT

Figure 6:
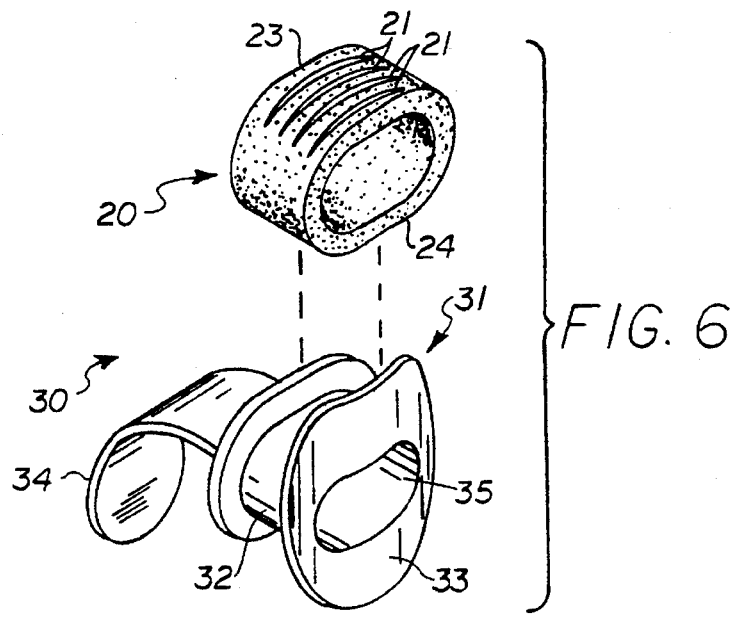
FIG. 6 is an exploded isometric view showing a mandibular protracting oral intubation mouthpiece or bite block having a resilient sleeve in accordance with another embodiment of the present invention.

Referring to the drawings by numerals of reference, there is shown a mandibular protracting oral intubating airway 10 in accordance with the present invention. FIG. 1 shows the mandibular protracting oral intubating airway 10 in an unassembled condition.

The mandibular protracting oral intubating airway 10 has a rigid main body 11 with a bite block or mouthpiece portion 12 at the forward end. The main body 11 is formed of polypropylene or other suitable material. The mouthpiece portion 12 has an annular front flange 13 and a bite portion 14 which extends rearwardly therefrom. The bite portion 14 is generally oval-shaped in transverse cross section and defines a generally oval-shaped opening 15 which extends longitudinally rearward a short distance. An annular rear flange 16 surrounds the rear end of the bite portion 14. The bottom wall 17 of the bite portion 14 extends rearwardly from the rear flange 16 and curves downwardly in a flat, generally C-shaped tongue retractor portion 18, as seen from the side, and terminates in a rounded bottom end 19.

The annular front flange 13 extends radially outward from the oval-shaped bite portion 14 and is shaped and dimensioned to overlie a patient's lips. In the preferred embodiment illustrated, the front flange 13 is a generally oval-shaped configuration with the major axis in the vertical plane and the minor axis in the horizontal plane and is curved slightly rearward about the vertical axis.

The oval shaped opening 15 is sized to accommodate most endoscopes and related medical instruments, such as a conventional fiberoptic intubating stylet with an attached endotracheal tube. The length and width of the C-shaped tongue retractor portion 18 is sufficient to hold the tip and mid portion of the tongue forward, thus preventing it from falling backward and obstructing the airway, but is sufficiently short so as not to reach the epiglottis or base of the tongue to reduce the possibility of an involuntary gagging, coughing, or vomiting reaction in the patient, and is sufficiently narrow to fit between the lower molars as it covers the tongue.

A resilient annular sleeve 20 is mounted on the main body 11 between the front and rear flanges 13 and 16, respectively, and encircles the bite portion 14. The front and rear flanges 13 and 16 retain the resilient sleeve 20 on the bite portion 14. In the preferred embodiment, the resilient sleeve is installed by stretching to fit over the rear flange 16 and then releasing it. The rear flange 16 is sufficiently small to insure patient comfort and prevent the resilient sleeve 20 from slipping off the bite portion 14.

A series of longitudinally spaced generally arcuate grooves 21 and 22 extend transversely across the exterior top and bottom surfaces 23 and 24, respectively, of the resilient sleeve 20. The sleeve 20 is sufficiently soft to prevent trauma to the teeth and gums. The grooves 21 and 22 are sized and shaped to receive the upper and lower teeth of the patient when the mandible is protracted. The number of grooves and the location of the top grooves 21 relative to the bottom grooves 22 is sufficient to provide several combinations of top and bottom grooves to allow for maximum mandibular protraction in most patients and accommodate the anatomical variations that may arise. In other words, the lower teeth are received in a bottom groove 22 which is offset in the vertical plane from the top groove 21 which receives the upper teeth. The depth of the grooves 21 and 22 is sufficient to prevent the teeth from slipping out of the grooves in the longitudinal direction of the resilient sleeve 20.

As shown in FIG. 5, the mandibular protracting oral intubating airway 10 is placed in the mouth of a patient P. Jaw thrust or chin lift is performed manually to pull the mandible or lower jaw forward relative to the maxilla or upper jaw to achieve maximum protraction. When the mandible or lower jaw is protracted, it pulls the base of the tongue B forward with it, so that it tends to obstruct the airway less. The mandibular protracting oral intubating airway 10 is now positioned such that the underside of the flat downwardly curved tongue retractor 18 engages the tip T and mid portion M of the tongue.

The upper and lower teeth UT and LT are placed into the appropriate top and bottom grooves 21 and 22 in the resilient sleeve 20 with the annular front flange 13 overlying the patient's lips L and protecting them. The depth of the grooves 21 and 22 protects the teeth and prevents them from slipping out of the grooves in the longitudinal direction of the resilient sleeve 20.

When properly positioned, the upper and lower teeth UT and LT are retained in the grooves 21 and 22 on the resilient sleeve 20 with the mandible at maximum protraction and the downwardly curved tongue retractor 18 holds the tip and mid portion of the tongue forward, thus preventing it from falling backward and obstructing the patient's airway. The rounded bottom end 19 of the tongue retractor 18 does not reach the epiglottis or the base of the tongue, thus reducing the possibility of an involuntary gagging, coughing, or vomiting reaction in the patient. From the foregoing description, it can be seen that the mandibular protracting oral intubating airway device maintains the airway of unconscious or sedated patients open to the greatest degree possible.

Once the mandibular protracting oral intubating airway has been installed in the patient's mouth, there is no need for the anesthesiologist to perform continuous manual chin lift or jaw thrust and his or her hands are free to perform other tasks. The mouthpiece portion 12 of the rigid main body 11 functions as a bite block and allows insertion of an endoscope E1 through the oval-shaped opening 15 for endoscopic examination of the upper gastrointestinal and respiratory tracts.

The device 10 also functions as an intubation guide for oral fiberoptic intubation using a fiberoptic stylet in patients who cannot be intubated using traditional direct laryngoscopy. The oval shaped opening 15 is sized to allow passage of most endoscopes and related medical instruments, such as a fiberoptic intubating stylet with an attached endotracheal tube E2. After the endotracheal tube E2 has been placed in the trachea, the mandibular protracting oral intubating airway device 10 can be left in place or removed from the mouth and pulled over the standard smaller diameter endotracheal tube and conventional tube connector.

The resilient sleeve 20 may also be installed on a tubular portion of other medical devices which are held in a patient's mouth between the patient's upper and lower teeth to accomplish mandibular protraction.

Figure 7:
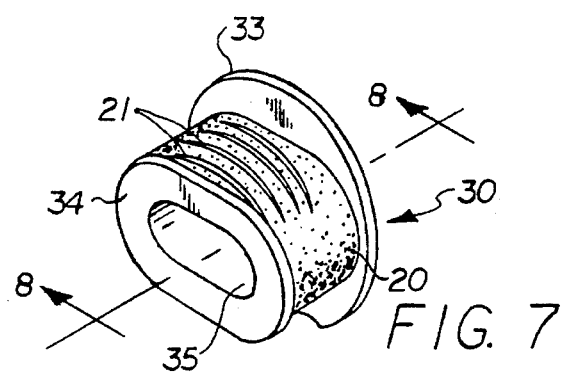
FIG. 7 is an exploded isometric view of the mandibular protracting oral intubation mouthpiece or bite block shown from the rear in an assembled condition.
Figure 8:
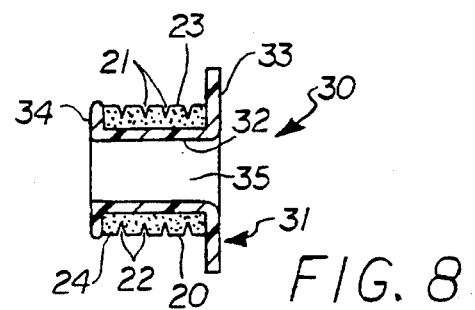
FIG. 8 is a cross sectional view of the mandibular protracting oral intubation mouthpiece or bite block taken along line 8—8 of FIG. 7.

For example, FIGS. 6–8 show the resilient tubular member 20 installed on a mandibular protracting oral intubation mouthpiece or bite block 30 formed of suitable rigid material such as polypropylene. The mouthpiece 30 has a rigid main body 31 with a bite portion 32, an annular front flange 33 at the forward end, and an annular rear flange 34 at the rearward end. In a preferred embodiment the bite portion 32 is generally oval-shaped in transverse cross section and defines a generally oval-shaped opening 35 therethrough.

The annular front flange 33 extends radially outward from the oval-shaped bite portion 32 and is shaped and dimensioned to overlie a patient's lips. In the preferred embodiment illustrated, the front flange 33 is a generally oval-shaped configuration with the major axis in the vertical plane and the minor axis in the horizontal plane and is curved slightly rearward about the vertical axis. The oval shaped opening 35 is sized to accommodate most endoscopes and related medical instruments, such as a fiberoptic intubating stylet with an attached endotracheal tube.

The resilient annular sleeve 20, is mounted on the main body 11 between the front and rear flanges 33 and 34, respectively, and encircles the bite portion 32. The front and rear flanges 33 and 34 retain the resilient sleeve 20 on the bite portion 32. In the preferred embodiment, the resilient sleeve 20 is installed by stretching to fit over the rear flange 34 and then releasing it. The rear flange 34 is sufficiently small to insure patient comfort and prevent the resilient sleeve 20 from slipping off the bite portion 32.

A series of longitudinally spaced generally arcuate grooves 21 and 22 extend transversely across the exterior top and bottom surfaces 23 and 24, respectively, of the resilient sleeve 20. The grooves 21 and 22 are sized and shaped to receive the upper and lower teeth of the patient when the mandible is protracted. The number of grooves and the location of the top grooves 21 relative to the bottom grooves 22 is sufficient to provide several combinations of top and bottom grooves to allow for maximum mandibular protraction in most patients and accommodate the anatomical variations that may arise. In other words, the lower teeth are received in a bottom groove 22 which is offset in the vertical plane from the top groove 21 which receives the upper teeth. The depth of the grooves 21 and 22 is sufficient to prevent the teeth from slipping out of the grooves in the longitudinal direction of the resilient sleeve 20.

The mandibular protracting oral intubation mouthpiece or bite block 30 is placed in the mouth of a patient. Jaw thrust or chin lift is performed manually to pull the mandible or lower jaw forward relative to the maxilla or upper jaw to achieve maximum protraction. When the mandible or lower jaw is protracted, it pulls the patient's tongue forward with it, so that it tends to obstruct the airway less. The upper and lower teeth of the patient are placed into the appropriate top and bottom grooves 21 and 22 in the resilient sleeve 20 with the annular front flange 13 overlying the patient's lips and protecting them. The depth of the grooves 21 and 22 protects the teeth and prevents them from slipping out of the grooves in the longitudinal direction of the resilient sleeve 20. When properly positioned, the upper and lower teeth are retained in the grooves 21 and 22 on the resilient sleeve 20 with the mandible at maximum protraction.

Once the mandibular protracting oral intubation mouthpiece or bite block 30 is placed in the mouth of a patient, an endoscope or other related medical instruments, such as a fiberoptic intubating stylet with an attached endotracheal tube, may be passed through the opening 35.

While this invention has been described fully and completely with special emphasis upon a preferred embodiment, it should be understood that within the scope of the appended claims the invention may be practiced otherwise than as specifically described herein.

I claim:

1. An airway device comprising:

a rigid tubular member(14) having rear and front flanges (16, 13), and an access port extending longitudinally through said tubular member, said front flange adapted to overlie a wearer's lips;

a resilient, annular tooth-engaging member (20);

mandible positioning means for positioning and maintaining a protracted mandibular position comprising a transversely arranged series of grooves on a top portion of said tooth-engaging member adapted to engage a wearer's upper teeth in a first position and a transversely arranged series of grooves on a bottom portion of said tooth-engaging member adapted to engage a wearer's lower teeth and position and maintain a wearer's mandible in a second, protracted position relative to said first position; and tongue positioning means for positioning and maintaining the wearer's tongue in a forward position that does not obstruct the wearer's airway comprising a rigid and curved rearward extension on said rigid tubular member which is adapted to engage the top of the wearer's tongue.

2. The airway device according to claim 1 in which;

said resilient, annular tooth-engaging member comprises an annular resilient sleeve on said rigid tubular member disposed between said rear and front flanges.

3. The airway device according to claim 1 in which;

said rigid and curved rearward extension is flat in transverse cross section and extends rearwardly from said rigid tubular member and curves downwardly relative thereto to form a generally C-shaped flat tongue retractor portion which engages the wearer's tongue.

4. The airway device according to claim 3 in which;

said C-shaped flat tongue retractor portion is dimensioned to hold the tip and mid portion of the tongue forward without touching the wearer's epiglottis and base of the tongue to reduce the possibility of an involuntary gagging, coughing, or vomiting reaction in the wearer.

5. The airway device according to claim 1 in which;

said rigid tubular member and said access port are generally oval-shaped in transverse cross section.

* * * * *